United States Patent [19]
Debabov et al.

[11] Patent Number: 6,132,999
[45] Date of Patent: Oct. 17, 2000

[54] L-THREONINE-PRODUCING MICROBACTERIA AND A METHOD FOR THE PRODUCTION OF L-THREONINE

[75] Inventors: Vladimir Georgievich Debabov; Uri Ivanovich Kozlov; Evgenyi Moiseevich Khurges; Vytalyi Arkadievich Lifshits; Nelli Isaakovna Zhdanova; Michail Markovich Gusyatiner; Alexander Konstantinovich Sokolov; Tatiana Alexandrovna Bachina; Andrei Yurevich Christoserdov; Uri Dmitrievich Tsigankov; Nikolai Kazimirovich Yankovsky; Sergi Vladimirovich Mashko; Alla Lvovna Lapidus; Oksana Fedorovna Gavrilova; Oleg Alexandrovich Rodionov, all of Moscow, Russian Federation

[73] Assignee: Ajinomoto Co., Inc., Tokyo, Japan

[21] Appl. No.: 09/010,110

[22] Filed: Jan. 21, 1998

Related U.S. Application Data

[63] Continuation of application No. 08/346,185, Nov. 22, 1994, abandoned, which is a continuation of application No. 08/210,777, Mar. 21, 1994, abandoned, which is a continuation of application No. 07/947,916, Sep. 21, 1992, abandoned.

[51] Int. Cl.$^7$ .............................. C07H 21/04; C12N 1/21; C12N 15/70; C12N 15/73; C12P 13/08
[52] U.S. Cl. ................. 435/115; 435/252.3; 435/252.33; 435/320.1; 536/23.2; 536/23.7
[58] Field of Search ................................ 435/115, 252.3, 435/252.33, 320.1, 69.1, 488; 536/23.2, 23.7, 24.1

*Primary Examiner*—David Guzo
*Assistant Examiner*—Thomas G Larson
*Attorney, Agent, or Firm*—Oblon, Spivak, McClelland, Maier & Neustadt, P.C.

[57] ABSTRACT

The present invention provides a novel microbial strain and a method for effectively producing L-threonine. The novel strain can grow on a medium containing molasses, a much cheaper raw material than sucrose. The exemplary novel strain *E. coli* BKIIM B-5318 bears the plasmid pPRT614, which has threonine biosynthesis genes (thr A, B and C), the expression of which is regulated by a lambda-phage PR promoter and temperature-sensitive C1 repressor. The present microorganism is prototrophic with regard to isoleucine. The strain *E. coli* BKIIM B-5318 produces more than 70 g/l of L-threonine when cultured at 38–41° C. for 32 hours in a medium containing molasses.

10 Claims, 4 Drawing Sheets

(FIG.1)
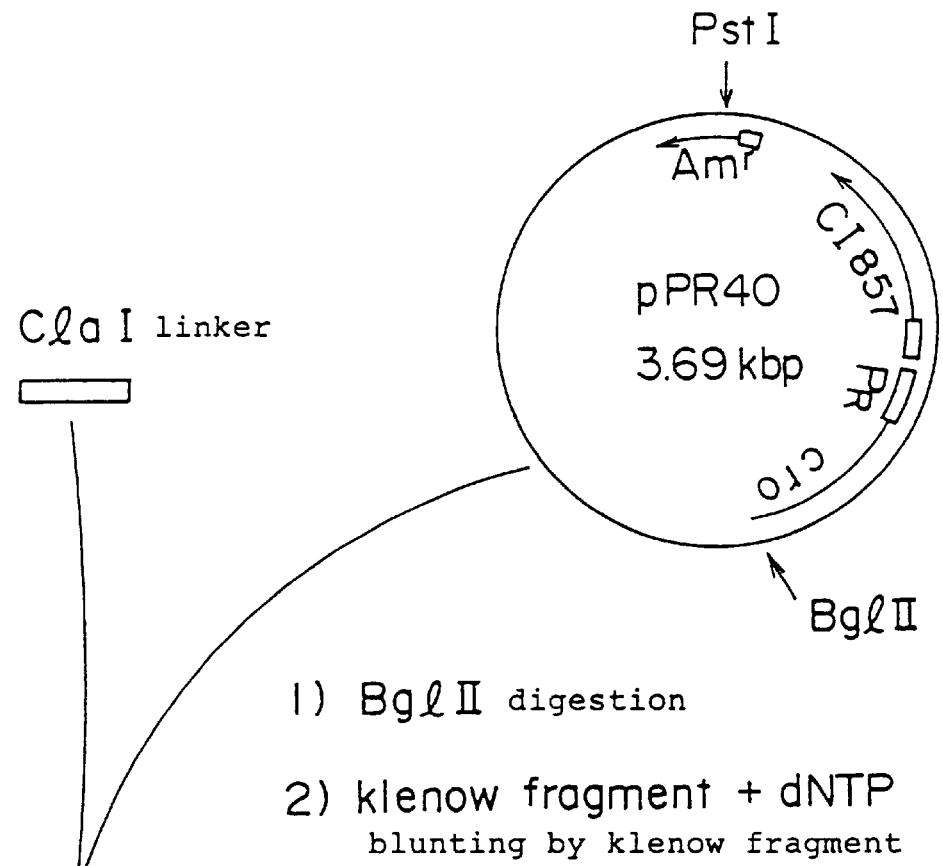
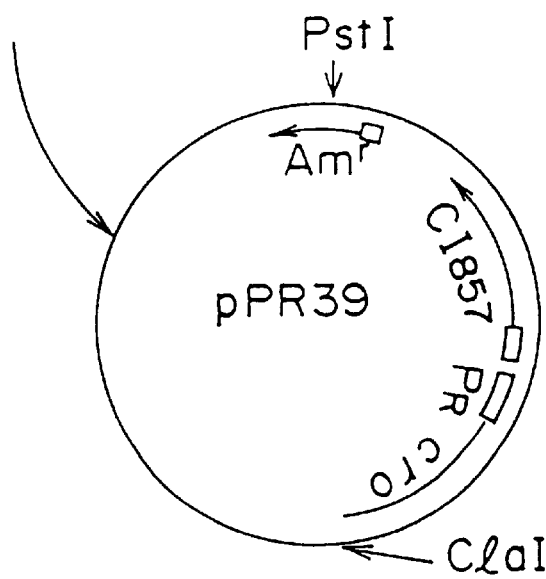

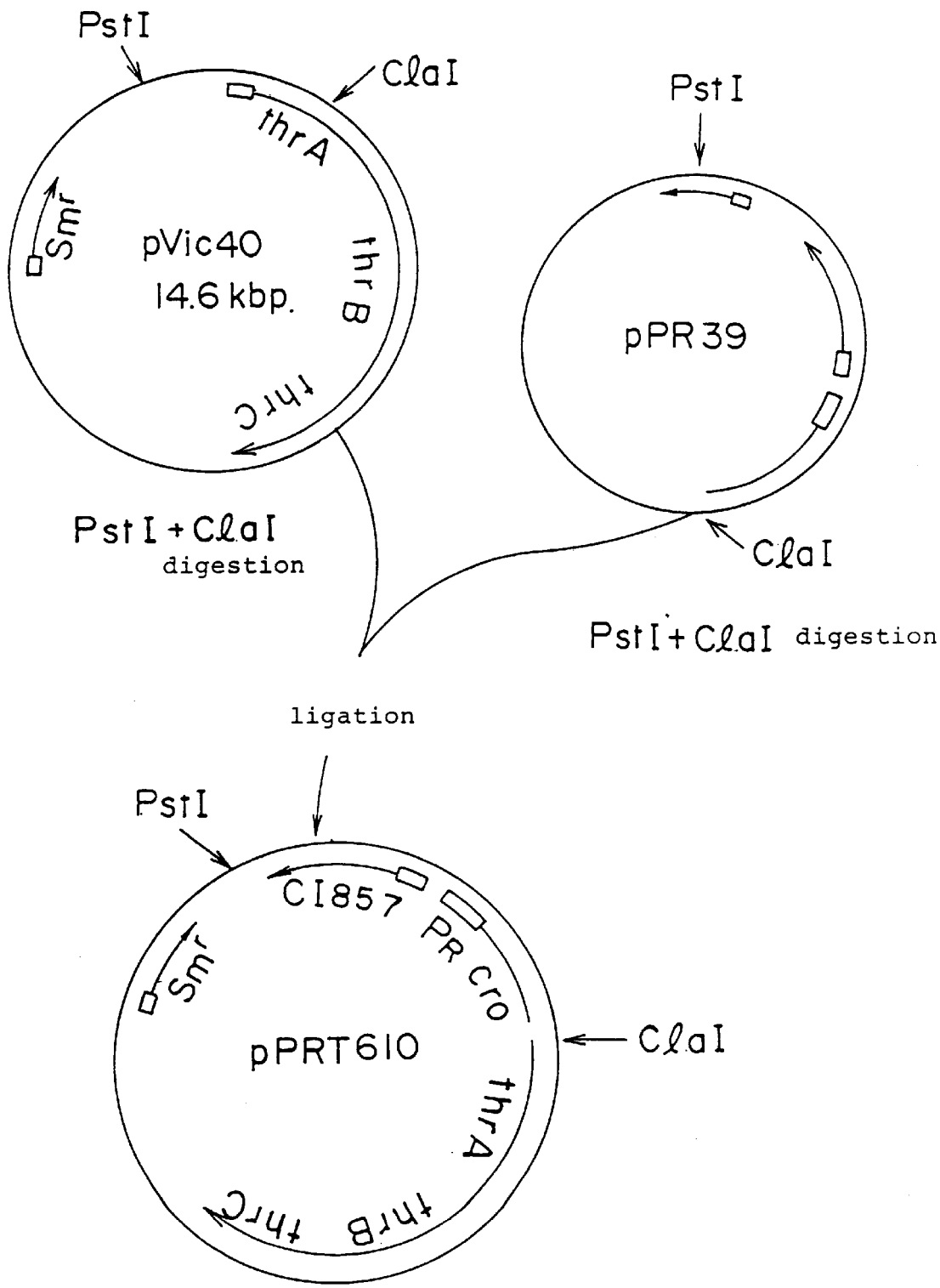
(FIG.2)

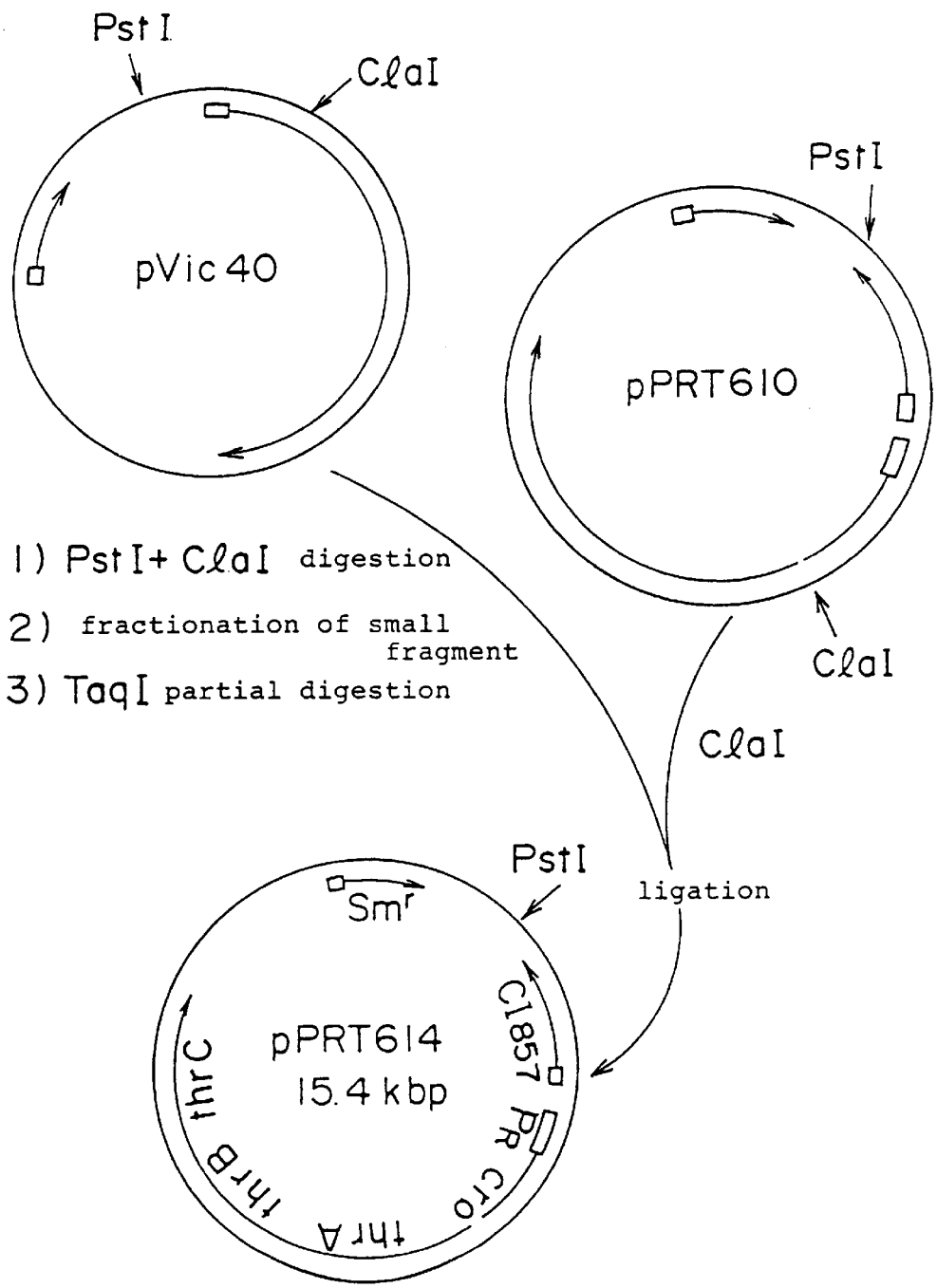
(FIG.3)

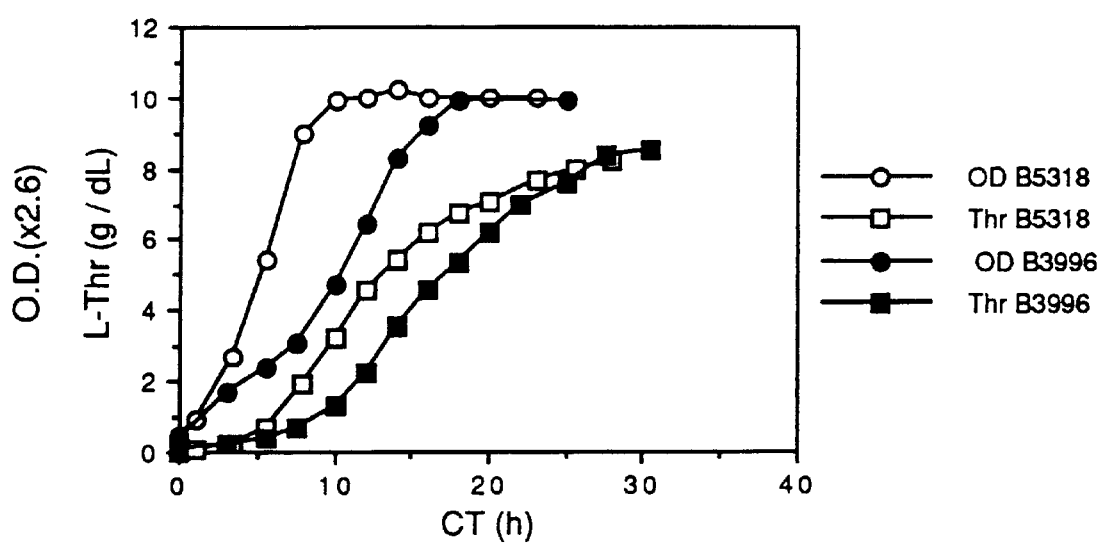
(Fig 4)

L-THREONINE-PRODUCING MICROBACTERIA AND A METHOD FOR THE PRODUCTION OF L-THREONINE

This application is a Continuation of application Ser. No. 08/346,185, filed on Nov. 22, 1994, now abandoned, which is a continuation of application U.S. Ser. No. 08/210,777 filed on Mar. 21, 1994, now abandoned, which is a continuation of application U.S. Ser. No. 07/947,916, filed on Sep. 21, 1992, now abandoned.

BACKGROUND OF THE INVENTION

1. Field of the Invention

The present invention is concerned with a novel microorganism and microbiological process for the production of L-threonine. L-threonine is an essential amino acid, used in various nutrient and medical compositions. Moreover, threonine is an important additive to animal fodder, a valuable reagent used in the pharmaceutical and chemical industries, and a growth factor for amino acid-producing microorganisms used in the production of, for example, lysine and homoserine.

2. Discussion of the Background

Prior to the present invention, natural strains of L-threonine-producing microorganisms and artificial mutants thereof have been used to fermentatively produce L-threonine. L-threonine-producing artificial mutants belonging to the genera Escherichia, Serratia, Brevibacterium and Corynebacterium are known, and most of them are resistant to α-amino-β-hydroxyvaleric acid. With respect to the genus Escherichia, methods for producing L-threonine using a strain transformed with a recombinant plasmid DNA comprising a threonine operon are shown in Japanese Laid-Open Patent Application Nos. 55-131397, 59-31691 and 56-15696, and in PCT Laid-Open Application No. 90-04636.

Primary carbon sources added to the fermentation media of these L-threonine-producing microorganisms include glucose, sucrose, starch hydrolysate and molasses. Based on (1) the level of threonine biosynthesis and (2) the expenditure coefficient, defined as the value (in g) of sugar necessary to produce 1 g of L-threonine, E. coli strain BKIIM B-3996 (hereafter "strain B-3996" or "B-3996") is the best of the strains disclosed (PCT Laid-Open Application No. 90-04636). Strain B-3996 can synthesize up to 85 g/l threonine, with an expenditure coefficient of 2 g sugar per 1 g of threonine, provided that a sugar-ammonium mixture is added to the nutrient medium (in response to a signal from the pH sensor used in a standard laboratory fermenter during cultivation).

However, most strains used to produce L-threonine, such as E. coli BKIIM B-3996, are L-isoleucine auxotrophic. Therefore, an enzyme in the pathway from L-threonine to L-isoleucine is defective. Accordingly, L-isoleucine must be added to cultures of L-threonine-producing strains. L-Isoleucine auxotrophy in L-threonine-producing strains prevents (1) by-production of isoleucine, thus decreasing L-threonine accumulation, and (2) surplus production of L-isoleucine, thus suppressing expression of the threonine operon(s) through the corresponding attenuator.

When using such an isoleucine-dependent strain, strict control of the amount of isoleucine added into a medium is required, because growth of the strain and threonine productivity must be moderately balanced. The more isoleucine added to the medium, the more the strain grows. However, threonine productivity is simultaneously repressed in an inverse manner.

From this point of view, strain B-3996 requires isoleucine (known as "leaky-type"), and as a result, exhibits low productivity of L-threonine in media containing molasses as both a carbon source and an energy source. Molasses is a non-nutrient raw material which is much cheaper than sucrose, but which also contains a high amount of amino acids (ex. isoleucine). Thus, although it is highly desired in the art to use molasses as both a carbon source and an energy source, the isoleucine present in molasses suppresses production of L-threonine in L-threonine-producing bacteria.

SUMMARY OF THE INVENTION

Accordingly, one object of the present invention is to provide a novel microorganism producing a high concentration of threonine.

A further object of the present invention is to provide a novel method for the fermentative production of threonine, in which a microorganism produces a high concentration of threonine in a medium containing molasses as a raw material.

These and other objects which will become apparent during the following detailed description of the preferred embodiments, are provided by a novel microorganism which produces a large number of generations and L-threonine when cultured in a medium containing molasses as a raw material, and a method of producing L-threonine using a novel microorganism in a medium containing molasses as a raw material.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a scheme for obtaining the plasmid pPR39;

FIG. 2 is a scheme for obtaining the plasmid pPRT610;

FIG. 3 is a scheme for obtaining the plasmid pPRT614;

FIG. 4 graphically profiles the growth curve and accumulation of L-threonine when culturing B-3996 and B-5318, wherein O represents the growth curve of B-5318, □ represents the accumulation of L-threonine when culturing B-5318, ● represents the growth curve of B-3996, and ■ represents the accumulation of L-threonine when culturing B-3996.

DETAILED DESCRIPTION OF THE PREFERRED EMBODIMENTS

The present inventors have achieved the goals of the present invention by providing the strain E. coli BKIIM B-5318, which produces up to 70 g/l of threonine during 32 hours of growth on a molasses medium. The expenditure coefficient of this strain is 1.7 as defined above).

The novel strain E. coli BKIIM B-5318 was obtained by transformation of a new recipient strain E. coli VNIIGenetika TDH-7 transformed with plasmid pPRT614. As shown in FIG. 3, plasmid pPRT614 was obtained by substituting the regulatory region of the threonine operon of plasmid pVIC40 for the PR promoter and temperature-sensitive lambda-phage C1 repressor. The pVIC40 TaqI-ClaI fragment is introduced into pPRT610, which is missing the upstream region of the thrA gene, lost during its production. As a result, pPRT614 is provided with an entire thrA gene (FIG. 3).

Plasmid pPR40 was the donor of the promoter and repressor (FIGS. 1, 2). FIG. 1 shows the introduction of the ClaI site (chemically synthesized by known methods) into the BglII site of pPR40 to produce pPR39. FIG. 2 shows digestion of both pVIC40 and pPR39 with both PstI and ClaI. By ligating the above fragments to locate the lambda-phage promoter and repressor upstream from the threonine operon, pPRT610 was prepared. However, the ClaI site is located in the coding region of thrA gene in pVIC40.

The new recipient strain E. coli VNIIGenetika TDH-7 is a isoleucine prototroph. It was obtained from plasmidless cells of strain VNIIGenetika TDH-6. E. coli VNIIGenetika TDH-6 is deposited in the Research Institute of Genetics and Industrial Microorganism Breeding at Russia 113545 Moscow, 1 Dorozhny Proezd., 1 (Registration No. BKIIM B-3420).

For this purpose, the plasmidless cells of strain E. coli VNIIGenetika TDH-6 were infected by phage P1, earlier propagated on cells of strain E. coli c6000. Thereafter, transductants were selected which were capable of growth on isoleucine-free media. The selected strain was designated E. coli VNIIGenetika TDH-7. TDH-7 was then transformed with plasmid pPRT614, leading to the establishment of the strain E. coli BKIIM B-5318.

The new strain E. coli BKIIM B-5318 differs from the known strain by the fact that it is capable of growth on enriched nutrient media (for example, on media with molasses), which leads to a more effective production of threonine. The difference in threonine production results from two modifications:

(1) A temperature-sensitive lambda-phage C1 repressor and PR promoter replaces the regulatory region of the threonine operon in plasmid pVIC40; and (2) Strain B-5318 is prototrophic with regard to isoleucine.

E. coli BKIIM B-5318 produces more than 70 g/l of threonine during 32 hours of fermentation on molasses, in standard laboratory conditions, and at temperatures of 38–41° C.

The new producers of threonine E. coli BKMIIM B-5318 was deposited in the collection of microorganism cultures of the All-Union Research Institute of Antibiotics (Registration No. 2070) and also in the Research Institute of Genetics and Industrial Microorganism Breeding at Russia 113545 Moscow, 1 Dorozhny Proezd., 1 (Registration No. BKIIM B-5318) on May 3, 1990.

The new strain E. coli BKIIM B-5318 has the following morphological and biochemical traits:

(1) Cell Morphology: Gram-negative; round-ended rods with low mobility, 1.5–2.0 $\mu$m in length.

(2) Characteristics of Cultures:

(A) Meat-Peptone Agar: After 24 hours of growth at 37° C. cultures form rounded, whitish, semi-transparent colonies with a diameter of 1.5–3.0 mm; the surfaces of the colonies are smooth, the edges are even or slightly wavy, the center of the colony is elevated, the structure is homogeneous, and the consistency is paste-like and easy to emulgate.

(B) Agar Luria: After 24 hours of growth at 37° C., cultures form whitish semi-transparent colonies 1.5–2.5 mm in diameter; the surface of the colonies is smooth, the edges are even, the structure homogeneous, and the consistency is paste-like and easily emulgated.

(C) Agarized Adams Medium: After 40–48 hours of growth at 37° C., cultures form colonies 0.5–1.5 mm in diameter; greyish-white, semi-transparent, slightly elevated with a shining surface.

(D) Growth on Meat-Peptone Broth: The specific rate of growth at 37° C. is 1.3 $h^{-1}$; after 24 hours of growth, a drastic homogeneous turbidity and characteristic odor are observed.

(3) Physico-Biochemical Traits: Growth along a prick of the meat-peptone agar is even along the entire prick. The microorganism is a facultative anaerobe. It does not liquify gelantine. Grows well on milk and causes milk coagulation. Does not form indole. Resistant to streptomycin. It is resistant to the potential product inhibitors L-threonine and L-homoserine.

Temperature-sensitivity: Grows on meat-peptone broth at 43° C. and lower. Optimal growth revealed at 37–38° C.

pH sensitivity: Grows on media at pH from 6.0 to 8.0; optimal pH=7.0.

Growth on different carbon sources: Grows well on sucrose, glucose, lactose, mannose, galactose, xylose, glycerol, mannite with the formation of acid and gas.

Growth on different nitrogen sources: Assimilates nitrogen in the form of ammonia, nitrates, and also nitrogen of some organic compounds.

Plasmid content: The cells comprise a multi-copy hybrid plasmid pPRT614 (mol. mass 10.2 MD) that provides streptomycin resistance and carries the threonine operon genes, the lambda-phage promoter and the temperature-sensitive repressor C1 gene.

The plasmid is highly stable in strain E. coli BKIIM B-5318, even during growth in the absence of selective pressure to maintain the plasmid. The stability of the strain characteristics provided by the plasmid were evaluated for strain E. coli BKIIM B-5318 (plasmid pPRT614) and for strain-prototype E. coli BKIIM B-3996 (plasmid pVIC40). The cells of both strains were grown in the presence of streptomycin until the onset of the early stationary stage. Cells were then seeded on Luria medium without antibiotic, at a starting titre 50. After 48 hours of cultivation at 36.7–40° C., the cells obtained were reseeded on Luria medium to the starting titre 50, and again cultivated for 48 hours at the same temperature. Each passage corresponded to 20 generations. After the indicated passages, the cells were seeded on Luria agar, and the colonies were checked for streptomycin resistance. In both strains, the proportion of plasmidless cells was less than 1%.

Production of L-Threonine

A culture of strain E. coli BKIIM B-5318 prepared as described above was grown on agarized Adams medium containing streptomycin. The suspension of cells was then seeded in liquid inoculum or fermentation medium, comprising sources of carbon, nitrogen, essential mineral salts and nutrient additives in the form of protein hydrolysates. (The presence of L-isoleucine in the fermentation medium is not necessary). The growth of the inoculum is carried out at pH 6.8–7.2 at a temperature of 36–38° C., with continuous aeration and stirring. The inoculum, or a suspension of cells washed off the agar, is used for inoculation of the fermentation medium.

The fermentation is carried out in fermenters equipped with a system for pH stabilization at pH 6.8–7.2 and at a temperature of 38–40° C., with continuous aeration and stirring. Aqueous ammonia, or carbon- and nitrogen-balanced molasses-ammonia nutrient additive are used as pH-stabilizing agents. The duration of fermentation depends on the inoculum dose and the level of growth factor enrichment of the fermentation medium, but generally varies from 24 to 60 hours.

The specific expense of carbon sources needed for the synthesis of 1 g of L-threonine (the expenditure coefficient) is 1.8 g. No accumulation of aminoacetone in the culture medium was observed.

Other features of the invention will become apparent in the course of the following descriptions of exemplary embodiments which are given for illustration of the invention and are not intended to be limiting thereof.

EXAMPLE 1

Cultures of strains *E. coli* BKIIM B-3996 (prototype) and *E. coli* BKIIM B-5318 were grown separately on agarized Adams medium containing sucrose (0.2%) and streptomycin (100 μg/ml) for two days, then suspended in a physiological solution. Inoculum medium (500 ml) was seeded with a sample of the suspension (10 ml; titre=$10^8$). The inoculum medium had the following composition (percentages are by weight): molasses—3%, ammonium sulfate—0.5%, dipotassium phosphate ($K_2HPO_4$)—0.2%, magnesium sulfate heptahydrate ($MgSO_4.7H_2O$)—0.04%, ferrous sulfate ($FeSO_4.7H_2O$)—0.002%, manganese (II) sulfate ($MnSO_4.5H_2O$)—0.002%, yeast autolysate—0.2%, water—the remaining balance.

The inoculum is grown for 20 hours in a laboratory fermenter (vol. 0.7 l), with aeration (0.5 l/min) and stirring (1200 rotations/min) at a temperature of 39° C. The pH was maintained in the range 6.9–7.2 by an automatic inlet providing a molasses-ammonium nutrient additive (a mixture of ammonium water and molasses in a molar ratio 2.92:1, with a molasses concentration in the mixture of 300 g/l). Fermentation was carried out for 32 hours.

The results are given in Table 1 below:

TABLE 1

| Strain | Threonine concentration (g/l) | Expenditure coefficient (g sugar consumed / g threonine produced) |
|---|---|---|
| B-3996 | 46.7 | 2.5 |
| B-5318 | 70.4 | 1.7 |

Note: Accumulation of threonine and the expenditure coefficient for strains BKIIM B-3996 and BKIIM B-5318 after 32 hours fermentation using molasses.

After 32 hours, *E. coli* BKIIM B-5318 produces 70.4 g/l L-threonine, whereas the prototype strain B-3996 produces only 46.7 g/l L-threonine. The corresponding expenditure coefficients are 1.7 and 2.5, respectively.

Thus, the present microorganism increases the output of L-threonine in fermentation media containing molasses in comparison to the prototype strain, while the expenditure coefficient is simultaneously lowered.

EXAMPLE 2

Strains *E. coli* BKIIM B-3996 (prototype) and *E. coli* BKIIM B-5318 were grown separately on agarized M9 medium containing 0.2% of sucrose and 100 μg/ml of streptomycin for 1 day, then suspended in an inoculum medium shown in Table 2. A sample of the suspension having a titre of $10^8$ (1 ml) was used to seed 250 ml of an inoculum medium prepared by dissolving the ingredients shown in Table 2 into 1 l of water.

TABLE 2

| ammonium sulfate ($(NH_4)_2SO_4$) | 5 (g/l) | 0.5 (%) |
|---|---|---|
| dipotassium phosphate ($K_2HPO_4$) | 2 | 0.2 |
| sodium chloride (NaCl) | 0.6 | 0.06 |
| magnesium sulfate ($MgSO_4.7H_2O$) | 0.4 | 0.04 |
| ferrous sulfate ($FeSO_4.5H_2O$) | 0.02 | 0.002 |
| manganese sulfate ($MnSO_4.5H_2O$) | 0.02 | 0.002 |

TABLE 2-continued

| yeast autolysate | 2 | 0.2 |
|---|---|---|
| sucrose (autoclaved-separately) | 30 | 3.0 |

The inoculum was grown for 12 hours in a laboratory fermenter (volume=1.0 l) with aeration (0.25 l/min) and stirring (700 rotations/min at first, then set to keep the oxygen pressure at a level of more than 2%) at a temperature of 39° C. The pH was maintained in the range of 6.7–7.1 by an automatic inlet providing ammonium gas. After fermentation, 25 ml of the culture was added to 250 ml of a fermentation medium. The contents of the fermentation medium are shown in Table 3.

TABLE 3

| ammonium sulfate ($(NH_4)_2SO_4$) | 4.5 (g/l) | 0.45 (%) |
|---|---|---|
| dipotassium phosphate ($K_2HPO_4$) | 1.8 | 0.18 |
| sodium chloride (NaCl) | 0.6 | 0.06 |
| magnesium sulfate ($MgSO_4.7H_2O$) | 0.36 | 0.036 |
| ferrous sulfate ($FeSO_4.5H_2O$) | 0.018 | 0.0018 |
| manganese sulfate ($MnSO_4.5H_2O$) | 0.018 | 0.0018 |
| yeast autolysate | 1.8 | 0.18 |
| sucrose (autoclaved separately) | 27 | 2.7 |
| antifoam agent (autoclaved separately) | 1 ml/l | |

The inoculum in the fermentation medium was grown for 28 hours in a laboratory fermenter (volume=1.0 l) with aeration (0.25 l/min) and stirring (700 rotations/min at first, then set to keep the oxygen pressure at a level of more than 2%) at a temperature of 39° C. The pH was maintained in the range of 6.7–7.1 by an automatic inlet providing ammonium gas. The sucrose concentration of the medium was maintained below 20 g/l by adding 600 g/l (60%) of an aqueous sucrose solution. The growth curve and L-threonine accumulation profiles are shown in FIG. 4, the fermentation results are shown in Table 4.

TABLE 4

| strain | accumulation of L-threonine (g/dl) | yield to sugar (%) | expenditure coefficient (g sugar/ g threonine) | culturing time (hr) |
|---|---|---|---|---|
| B-3996 | 8.3 | 40 | 2.4 | 30.0 |
| B-5318 | 8.2 | 41 | 2.4 | 28.0 |

As is apparent from Table 4, B-5318 is superior to B-3996 in growth speed. Thus, the culturing time can be shortened and contamination can be prevented.

What is claimed as new and desired to be secured by Letters Patent of the United States is:

1. A DNA, comprising:
   (a) a first DNA fragment comprising a gene encoding a lambda-phage temperature-sensitive C1 repressor, and PR promoter; and
   (b) a second DNA fragment, directly downstream from the first DNA fragment, comprising the *Escherichia coli* thrABC operon which contains a defective inherent transcription regulative region attenuator,
   wherein said C1 repressor and said PR promoter regulate expression of said *Escherichia coli* thrABC operon.

2. The DNA of claim 1, further comprising an RSF 1010 origin of replication and a selectable.

3. The DNA of claim 1, wherein said selectable marker gene is a gene providing streptomycin resistance.

4. The DNA of claim 1, wherein said DNA is pPRT614.

5. A microorganism transformed with DNA comprising:
   (a) a first DNA fragment comprising a gene encoding a lambda-phage temperature-sensitive C1 repressor and PR promoter; and
   (b) a second DNA fragment, directly downstream from the first DNA fragment, comprising the *Escherichia coli* thrABC operon which contains a defective inherent transcription regulative region attenuator,
   wherein said C1 repressor and said PR promoter regulate expression of said *Escherichia coli* thrABC operon;
   wherein said microorganism is an isoleucine prototroph belonging to the genus Escherichia.

6. The microorganism of claim 5, wherein said DNA is pPRT614 and the microorganism prior to transformation is *E. coli* VNIIGenetica TDH-7.

7. A method for producing L-threonine, which comprises the steps of:
   (A) culturing a microorganism which is an isoleucine prototroph belonging to the genus Escherichia transformed with DNA comprising:
      (a) a first DNA fragment comprising a gene encoding a lambda-phage temperature-sensitive C1 repressor and PR promoter; and
      (b) a second DNA fragment, directly downstream from the first DNA fragment, comprising the *Escherichia coli* thrABC operon which contains a defective inherent transcription regulative region, attenuator,
   wherein said C1 repressor and said PR promoter regulate expression of said *Escherichia coli* thrABC operon in a medium;
   (B) accumulating said L-threonine in the medium and said microorganism; and
   (C) collecting said L-threonine from the medium and said microorganism.

8. An isolated plasmid DNA, comprising:
   (a) a first DNA fragment comprising a gene encoding a lambda-phage temperature-sensitive C1 repressor and PR promoter; and
   (b) a second DNA fragment, directly downstream from the first DNA fragment, comprising the *Escherichia coli* thrABC operon which contains a defective inherent transcription regulative region attenuator,
   wherein said C1 repressor and said PR promoter regulate expression of said *Escherichia coli* thrABC operon, and wherein upon transformation of an isoleucine prototroph belonging to the genus Escherichia with said plasmid DNA, said isoleucine prototroph produces high levels of L-threonine using molasses as a carbon source.

9. A microorganism transformed with the isolated plasmid DNA of claim 8, wherein said microorganism is an isoleucine prototroph belonging to the genus Escherichia.

10. A method for producing L-threonine, which comprises the steps of:
   (A) culturing a microorganism transformed with the plasmid DNA of claim 8;
   (B) accumulating said L-threonine in the medium and said microorganism; and
   (C) collecting said 1-threonine from the medium and said microorganism.

* * * * *